United States Patent
Kobayashi et al.

(10) Patent No.: US 9,034,270 B2
(45) Date of Patent: May 19, 2015

(54) PLASMA STERILIZATION AND CLEANING TREATMENT DEVICE FOR ESCALATOR, AND ESCALATOR USING THE SAME

(75) Inventors: Hiroyuki Kobayashi, Kodaira (JP); Takumi Tandou, Hachioji (JP); Naoshi Itabashi, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 705 days.

(21) Appl. No.: 13/342,726

(22) Filed: Jan. 3, 2012

(65) Prior Publication Data

US 2012/0241284 A1    Sep. 27, 2012

(30) Foreign Application Priority Data

Mar. 22, 2011  (JP) .................. 2011-063320

(51) Int. Cl.
*B01J 19/08* (2006.01)
*B66B 23/24* (2006.01)
*B66B 31/02* (2006.01)
*A61L 2/14* (2006.01)

(52) U.S. Cl.
CPC .. *B66B 31/02* (2013.01); *A61L 2/14* (2013.01)

(58) Field of Classification Search
CPC ................................. A61L 2/14; B66B 31/02
USPC ..................................... 422/186.21; 198/335
See application file for complete search history.

(56) References Cited

U.S. PATENT DOCUMENTS

| | | | |
|---|---|---|---|
| 7,134,539 B2 | 11/2006 | Kim | |
| 8,557,187 B2 | 10/2013 | Ehlbeck et al. | |
| 2010/0292757 A1 | 11/2010 | Ehlbeck et al. | |

FOREIGN PATENT DOCUMENTS

| | | |
|---|---|---|
| JP | 9-278340 A | 10/1997 |
| JP | 2006-193319 A | 7/2006 |
| JP | 2007-520402 A | 7/2007 |
| JP | 2010-536131 A | 11/2010 |

OTHER PUBLICATIONS

English translation of Japanese Office Action dated May 27, 2014 (Six (6) pages).

*Primary Examiner* — Kevin Joyner
(74) *Attorney, Agent, or Firm* — Crowell & Moring LLP

(57) ABSTRACT

Sterilization and cleaning of an escalator hand rail are performed. A sterilization and cleaning device including a hand rail; a plasma source for irradiating the hand rails with ions or radicals or UV light; an enclosure for housing the plasma source; a power source for generating plasma; a fan for generating relatively negative pressure in the enclosure; filter units for removing removed bacteria, viruses, and organic matters such as hand marks; and filter plates located backward and forward of a moving direction of the hand rail in the enclosure along the hand rail is provided.

20 Claims, 12 Drawing Sheets

57-L  60  57-R  58

57-A(R,L)  57-B(R,L)  57-C(R,L)

POSITIONAL INFORMATION OF STAIN

LEVEL OF STAIN

POSITION IN LENGTH DIRECTION OF HAND RAIL

SETTING OF PLASMA INTENSITY

PLASMA INTENSITY

POSITION IN LENGTH DIRECTION OF HAND RAIL

PLASMA STERILIZATION AND CLEANING TREATMENT DEVICE FOR ESCALATOR, AND ESCALATOR USING THE SAME

CLAIM OF PRIORITY

The present application claims priority from Japanese patent application JP 2011-063320 filed on Mar. 22, 2010, the content of which is hereby incorporated by reference into this application.

FIELD OF INVENTION

The present invention relates to a plasma sterilization and cleaning treatment device for an escalator which sterilizes and cleans an escalator hand rail using plasma, and an escalator using the same.

BACKGROUND OF THE INVENTION

Generally, escalator hand rails are periodically cleaned by rag wiping. A device automatically wiping a hand rail part with a rag is suggested with increase in requirement for removing bacteria, viruses, and stains such as hand marks attached to the hand rail part. According to U.S. Pat. No. 7,134,539B2, a method for irradiating escalator hand rails with UV light for the purpose of sterilization is suggested. According to US2010/0292757A1, a method and a device for dry cleaning or sterilizing escalator hand rails using plasma which is generated by using process gas under atmospheric pressure atmosphere.

SUMMARY OF THE INVENTION

In the case of employing rag wiping as cleaning means for escalator hand rails, even when bacteria and viruses attached to the hand rails are removed, the bacteria and viruses attached to the rag may eventually be spread to entire circumference of the hand rails, if the rag is not frequently replaced. In addition, a cleaning method which has an aggressive sterilizing function is desirable if possible because the wet rag wiping itself has no sterilization effect. On the other hand, sufficient sterilization effect of the hand rails may not be obtained by UV light irradiation. Incomplete removal of organic matters such as hand marks is also a problem which should be solved.

A device disclosed in FIG. 21 of US2010/0292757A1 includes a gas nozzle for supplying plasma and a suction part which is arranged close to the gas nozzle and sucks out dust and ozone. The device generates plasma using process gas under the atmosphere, and dust and ozone generated by the plasma and flown apart are recovered by the suction part. In such a method, substances being undesirable for humans such as ozone and nitrogen oxides which are flown apart in the atmosphere by plasma irradiation are difficult to surely recover.

The present invention aims to provide a plasma sterilization and cleaning treatment device for an escalator which can sterilize and clean escalator hand rails and can minimize flying apart of undesired substances in the atmosphere, and an escalator using the device.

A representative aspect of the present invention is as follows. A plasma sterilization and cleaning treatment device for an escalator includes a plasma source having a planar discharge part arranged along a surface shape of an escalator hand rail and along a moving direction of the hand rail; an enclosure for housing the plasma source in encapsulated space; a pair of inlet parts located in the enclosure so as to communicate the encapsulated space to the outside atmosphere along the moving direction of the hand rail; filter plates arranged at the pair of the inlet parts, having a shape along a cross sectional surface shape of the hand rail, and having a microgap between the filter plate and the surface of the hand rail; and a power source for the plasma source, wherein the plasma source generates plasma close to the surface of the hand rail in an almost atmospheric pressure atmosphere; and wherein the filter plate has a filter for removing radicals generated in the space by the plasma and organic matters on the hand rail removed by the plasma.

According to the aspects of the present invention, cleanliness of the hand rail can be improved because bacteria and viruses attached to hand rails can be detoxificated and the detoxificated bacteria and viruses and hand marks can be removed by radicals generated by plasma.

DETAILED DESCRIPTION OF THE PREFERRED EMBODIMENT

According to a representative embodiment of the present invention, a sterilization and cleaning device having a hand rail, a plasma source for irradiating the hand rail with ions or radicals or UV light, an enclosure for housing the plasma source, a power source for generating the plasma, a fan for generating relatively negative pressure in the enclosure, and a filter for removing removed bacteria, viruses, and organic matters such as hand marks are located to an escalator. Thereby, the escalator hand rail can be sterilized and cleaned.

Hereinafter, a plasma sterilization and cleaning device in which the present invention is specifically applied to an escalator hand rail is described in detail with referring the drawings.

First Embodiment

Figure 1A:
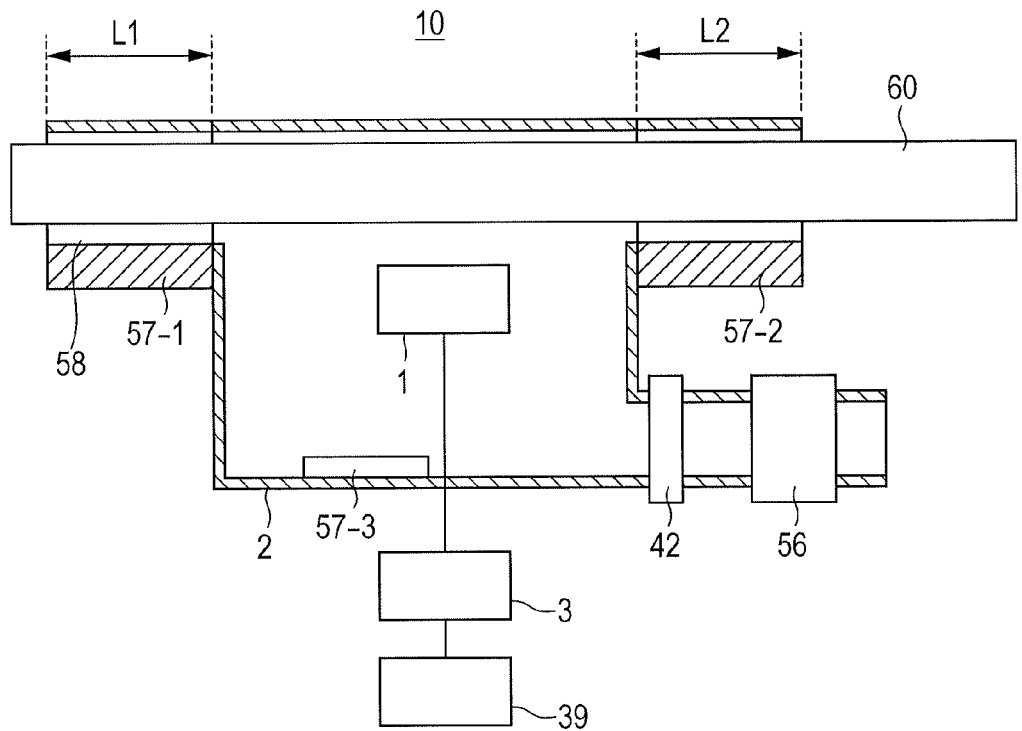
FIG. 1A is a view schematically showing entire constitution of a sterilization and cleaning device for an escalator hand rail according to a first embodiment of the present invention.
Figure 1B:
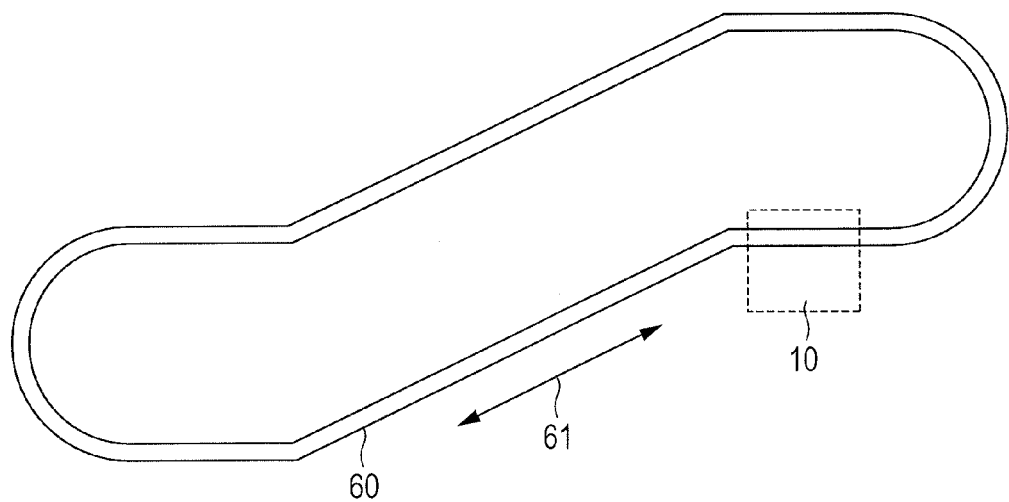
FIG. 1B is a view showing a constitution example of the hand rail in the first embodiment.

First, a first embodiment of the present invention is described. FIG. 1A schematically shows entire constitution of a sterilization and cleaning device for an escalator hand rail in the first embodiment. FIG. 1B is a view showing a constitution example of the hand rail in the first embodiment.

A plasma sterilization and cleaning unit 10 of the present invention is located in a predetermined position in the escalator such as a position where an escalator hand rail 60 is subducted to a lower side as shown in FIG. 1B. The plasma sterilization and cleaning unit 10 includes a plasma source 1 having a planar discharge part and an enclosure 2 which houses the plasma source into an internal encapsulated space. The plasma source 1 in the enclosure 2 is located facing to the escalator hand rail. A power source 3 for plasma generation is connected to the plasma source 1. A pair of filter plates 57-1 and 57-2 is located at both sides of the enclosure 2 to a moving direction of the hand rail. More specifically, the enclosure 2 has a pair of inlet parts located along a Moving direction of the hand rail 60 so as to communicate the encapsulated space to the outside atmosphere, and each of the pair of the filter plates 57 (57-1, 57-2) arranged between the filter plates and the surface of the hand rail through a microgap 58 at both inlet parts of the enclosure 2. A fan 42 and a filter box 56 are located inside of the enclosure 2. A filter plate 57-3 is located inside of the enclosure 2. The filter box 56 and the filter plates 57 include at least an absorbent such as activated carbon and an ozone decomposition catalyst. The enclosure 2 is constituted to be able to disassemble and the filter box 56 and the filter plate 57 can be periodically replaced.

Figure 2A:
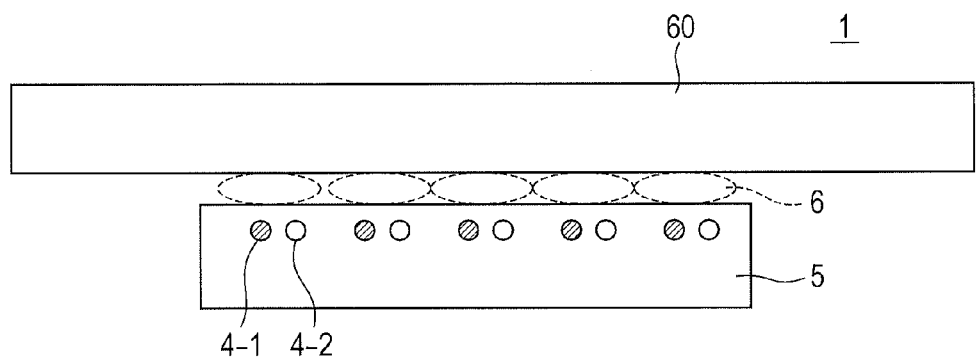
FIG. 2A is a cross-sectional view showing an example of a plasma source in the first embodiment.
Figure 2B:
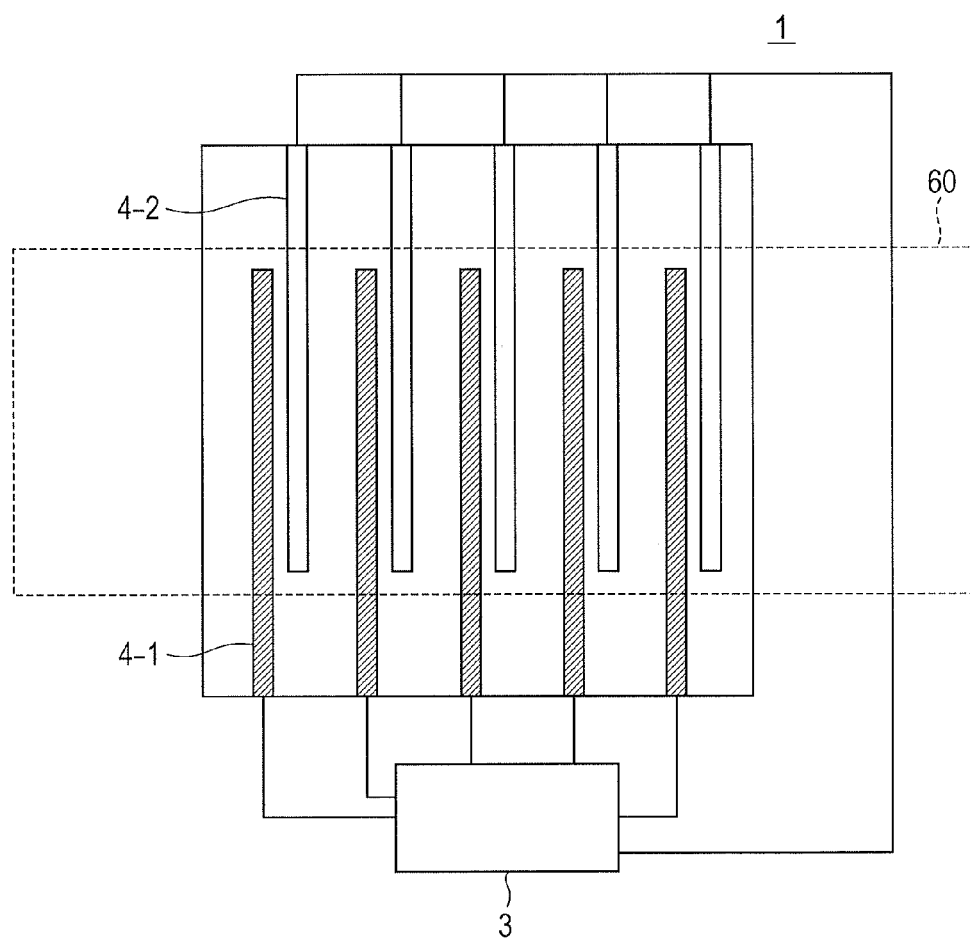
FIG. 2B is a schematic view of the plasma source in FIG. 2A seen in a vertical direction to a discharge surface.

In this embodiment, the escalator hand rail 60 is possible to move in either direction of right and left as shown by an arrow 61 in FIG. 2B. A reference numeral 39 represents a control computer. The control computer 39 controls drive of the hand rail 60 and steps (not illustrated) by a motor (not illustrated). The computer 39 also controls the power source 3 depending on an operation state of the escalator and controls plasma discharge to the hand rail. Rotation of the fan is also controllable by the control computer 39. More specifically, the control computer 39 starts plasma discharge from the plasma source 1 and starts up the fan 42 when the escalator starts. In addition, the control computer 39 terminates plasma discharge when the escalator stops, and then terminates the fan 42 after passing predetermined time.

Lengths L1 and L2 of the filter plates 57-1 and 57-2 are approximately the same length because the escalator moves either direction of right and left (climbing and descending).

In order to make the filter 56 exert a main function as a filter during operation, it is desirable that gas flow in the enclosure 2 is not disturbed by locating the filter plate 57-3 to a region where gas flow in the enclosure 2 is low.

Subsequently, the plasma source 1 is described using FIGS. 2 (FIG. 2A and FIG. 2B). FIG. 2A schematically shows a cross sectional surface of the plasma source and FIG. 2B schematically shows the plasma source seen in a vertical direction to a discharge surface. The plasma source 1 of the present invention has a planar discharge part and has a comb-shaped structure in which a plurality of electrodes 4-1 and 4-2 are alternately arranged in a dielectric body 5. For example, an electrode 4-1 as an antenna and an electrode 4-2 as a grounding wire function as a pair of electrodes.

The plasma source 1 includes a discharge plate constituting the planar discharge part and a high-frequency power source 3 for plasma generation. The discharge plate is constituted by the dielectric body 5 made of quartz glass or a ceramic material such as alumina and yttria and a pair of electrodes 4-1 and 4-2 arranged inside of the dielectric body.

The pair of the electrodes 4-1 and 4-2 has a structure in which multiple insulated comb-shaped electrodes are alternately arranged parallel to each other in a rectangular region. These pairs of the electrodes are connected to the high-frequency power source 3. The pair of the electrodes 4-1 and 4-2 has a length corresponding to a width of the hand rail 60. High frequency radiation is applied to the pair of the electrodes 4-1 and 4-2 so that the electrodes have different polarity each other or one electrode has ground potential. Thereby, plasma 6 is generated close to the surface of the dielectric body 5 by dielectric barrier discharge. The plasma is generated close to the surface of the dielectric body film along between the electrode 4-1 and the electrode 4-2. In other words, the plasma 6 is generated close to the surface of the hand rail 60 by the planar discharge plate arranged along the moving direction of the hand rail 60. As a result, the surface of the hand rail 60 can be irradiated with this plasma.

In the rectangular region, the plurality of the electrodes 4-1 and 4-2 are divided into a plurality of small regions and is connected to the high-frequency power source 3, and thereby the high-frequency power source can be controlled so as to supply electric power from the high-frequency power source 3 to the whole electrode pairs or at least electrode pairs in one small region. Thereby, discharge area of the plasma at the surface of the hand rail 60 can be adjusted.

Close to the electrodes 4-1 and 4-2, a pair of cuspidate metal electrodes for corona discharge and a high-frequency power source (not illustrated) is desirably located as an ancillary plasma source for ignition. The ancillary plasma is formed by corona discharge by the ancillary plasma source. The ancillary plasma can be useful as long as the ancillary plasma has ability to sufficiently supply charged particles or particles in an excited state to trigger discharge for generating the plasma 6 by the electrodes 4-1 and 4-2. Alternatively, a power source of plasma may be a direct-current power source.

Figure 3:
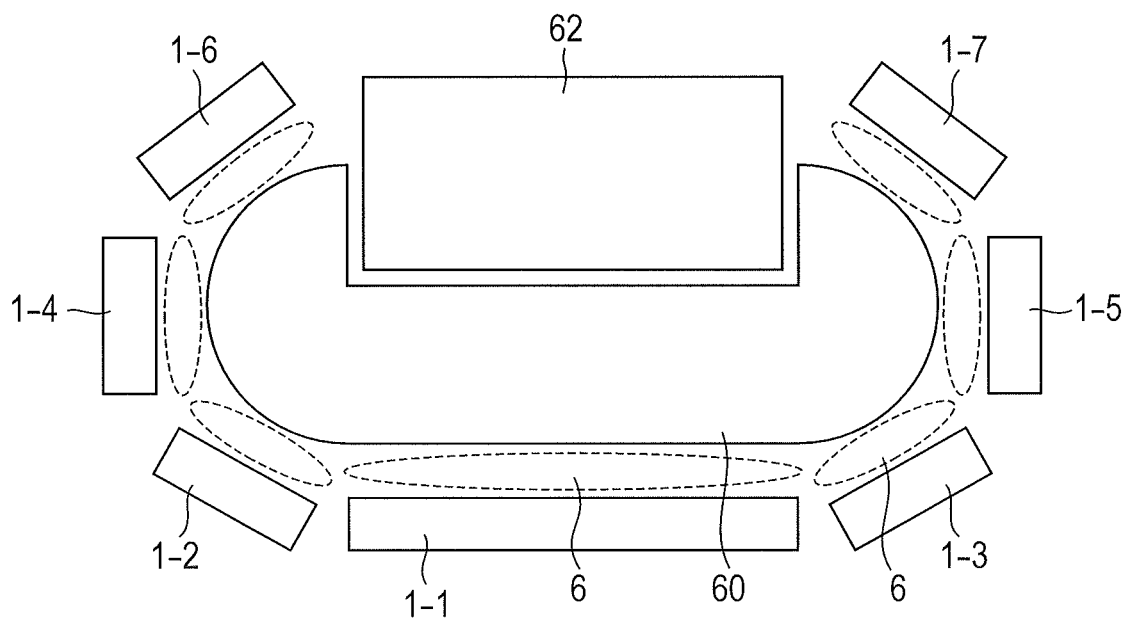
FIG. 3 is a view showing an example of a method for arranging the plasma source in the first embodiment.

One example of a method for arranging a flat-type plasma source 1 is shown in FIG. 3. A reference numeral 62 represents a guide of the hand rail. When the flat-type plasma source is used, the plasma source 1 is desirably located so as to cover entire outer surface of the hand rail 60 except the part of the guide 62 by dividing the plasma source 1 into a plurality of plasma sources 1-1 to 1-7 and locating them.

Figure 4A:
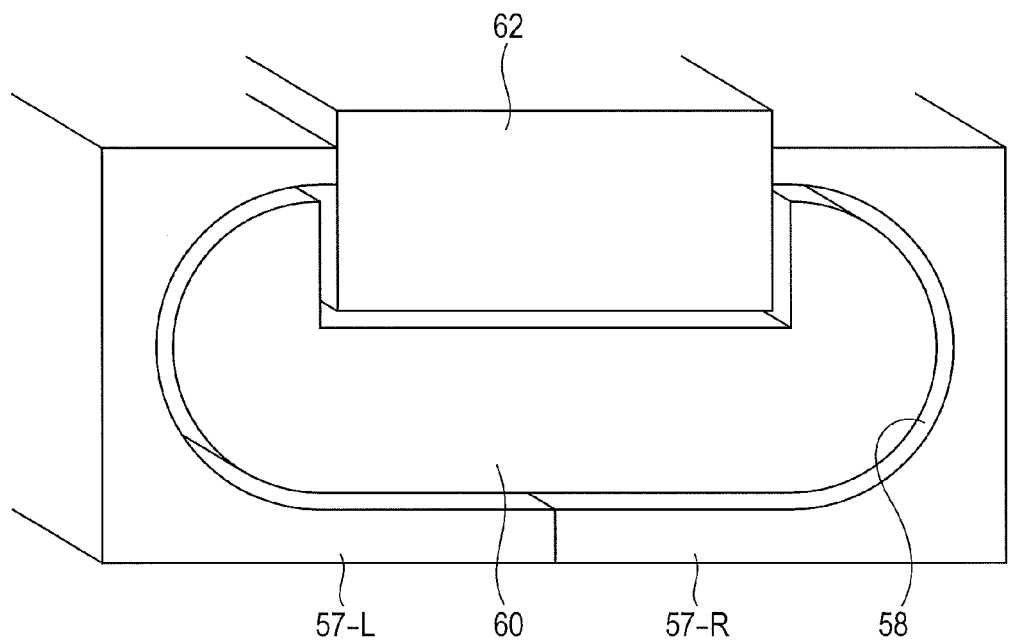
FIG. 4A is a schematic view of a cross sectional surface of filter plates in a vertical direction to a moving direction of the hand rail in the first embodiment.
Figure 4B:
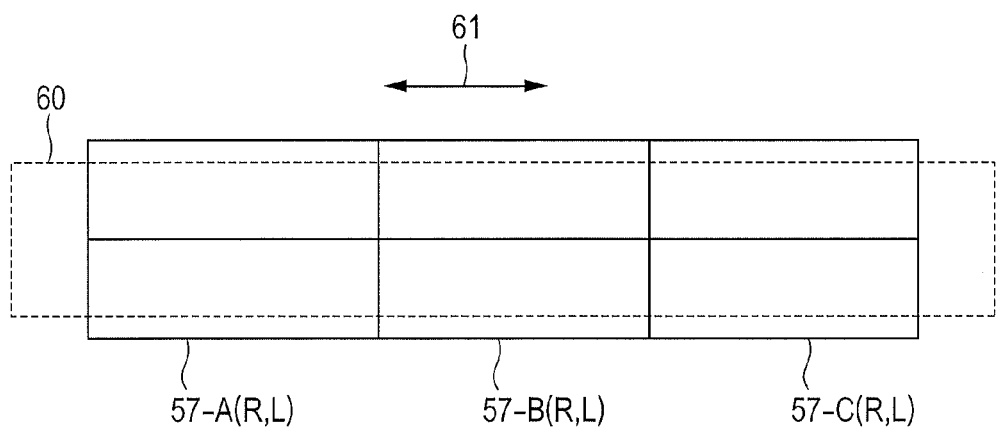
FIG. 4B is a schematic view showing filter plates along the moving direction of the hand rail in the first embodiment.

Subsequently, filter plates 57 (57-1 and 57-2) located along the hand rail 60 and in both sides to the plasma source 1 in the enclosure 2 are described using FIG. 4 (FIG. 4A and FIG. 4B). FIG. 4A is a schematic view showing a cross sectional surface of the filter plates in a vertical direction to the moving direction 61 of the hand rail. FIG. 4B is a schematic view showing the filter plates along the moving direction of the hand rail. A side of the filter plates 57 facing to the hand rail 60 has a structure in which the filter plates 57 is along a shape of the hand rail 60. A surface of the filter plates facing to the hand rail is constituted by an absorbent such as activated carbon and an ozone decomposition catalyst for absorbing activated species and removed and vaporized organic matters. The filter plates 57 have a structure in which two of a right side part 57-R and a left side part 57-L are combined. In this case, the enclosure 2 may be formed so as to have a single encapsulated space as a whole. Alternatively, the enclosure 2 may be constituted so as to have two right and left encapsulated spaces having each of the filter plates 57 and the plasma source 1 in each encapsulated space.

The filter plates 57 are divided into a plurality of filter plates 57-A, 57-B, and 57-C to the moving direction of the hand rail. Each of filter plates may be constituted so as to have different type of an absorbent and a catalyst located facing to the hand rail, surface roughness, or porosity.

Figure 5:
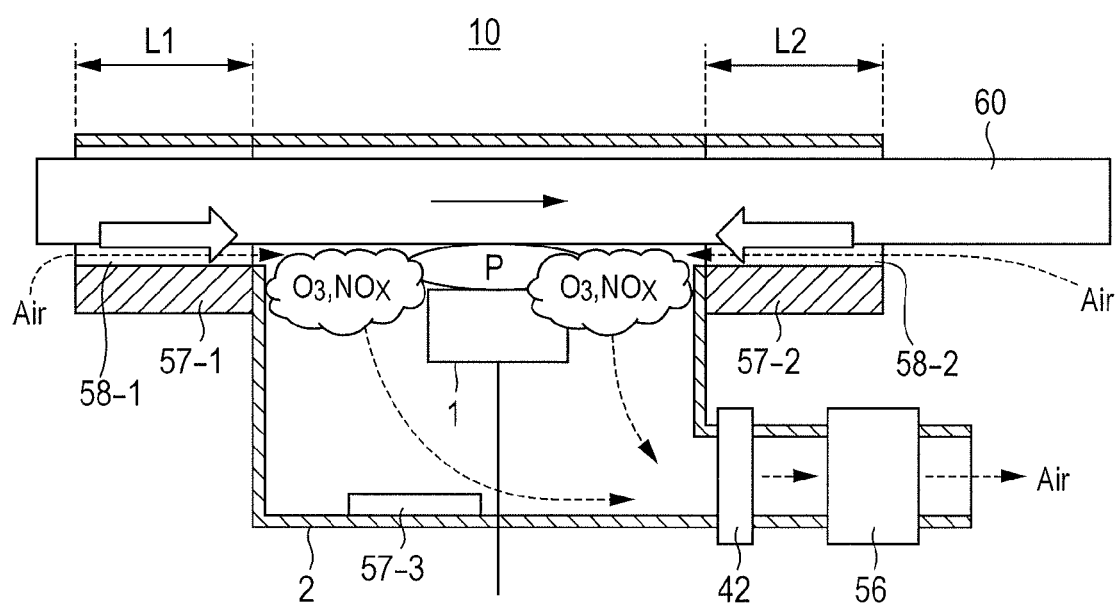
FIG. 5 is a view showing an operating state of the plasma sterilization and cleaning treatment device for the escalator in the first embodiment.

FIG. 5 is a view showing an operating state of the plasma sterilization and cleaning treatment device for the escalator of the present invention. Dashed lines in the view represent air flow.

Forcible ventilation is performed by rotating the fan 42 so that pressure in the enclosure 2 becomes slightly negative pressure to the surrounding atmosphere. Thereby, air is sucked from the surrounding atmosphere into the encapsulated space along the microgaps 58 (58-1 and 58-2) between the filter plates 57 and the hand rail 60. In this atmosphere, plasma is generated close to the surface of the hand rail 60 by the plasma source 1. Oxygen radical and other activated species generated by plasma irradiation to the hand rail 60 and other volatile matters are included in the enclosure collected by the fan 42 in almost atmospheric pressure air. However, these substances are removed through the filter 56 and forcibly ventilated into the atmosphere. In other words, radicals of oxygen and nitrogen in air and moisture (oxygen radical $O_3$, O radical, and OH radical) and electrons are generated by plasma, and bacteria and viruses attached to the surface of the hand rail 60 is detoxified by irradiating the hand rail 60 with these species. Organic matters such as hand marks attached to the hand rail are vaporized by radicals generated in plasma, UV light, and heat of plasma. With this phenomenon, activated species such as ozone, nitrogen oxides $NO_x$, detoxificated bacteria and viruses, hand marks, and other volatile matters are included in the air in the enclosure 2. These activated species and volatile matters included in the air in the enclosure are removed and exhausted to the atmosphere through the filter 56.

When the escalator stops by power failure or other accidents, the fan 42 usually stops too. At this time, unnecessary activated species such as oxygen radical $O_3$ and nitrogen oxides $NO_x$ and other volatile matters remaining in the enclosure 2 are absorbed by the filter plate 57-3. When the fan 42 stops, the air in the enclosure 2 is leaked outside through the microgap 58. At this time, the activated species and the other volatile matters remaining in the enclosure 2 are removed by the absorbent such as the activated carbon and the ozone decomposition catalyst in the filter plates 57-1 and 57-2. Thereby, flying apart of undesired substances such as ozone into the atmosphere can be suppressed.

FIG. 5 shows a state in which the hand rail 60 moves to a right direction in FIG. 5. In this case, when the left microgap 58-1 in which the moving direction of the hand rail 60 corresponds to an air suction direction is compared with the right microgap 58-2 in which the moving direction of the hand rail 60 is opposite to the air suction direction during operation of the escalator, the right microgap 58-2 has slightly higher possibility of outflow of the activated species from the enclosure 2 to the atmosphere. Values of a length and a gap of the microgaps 58-1 and 58-2 are required to set in consideration of this point. The length L of the filter plate 57 is preferably set to a relation of:

$$L \propto V \cdot G,$$

where a moving speed of the hand rail is V and a size of the microgap 58 is G.

In one example, a total length of the enclosure 2 is set to 1 m; a length of the plasma source 1 is set to 10 cm, and each of lengths L1 and L2 of filter plates 57-1 and 57-2 located right and left thereof are set to about 30 cm. At this time, when a moving speed V of the hand rail is set to standard speed, the microgap is preferably set to, for example, about 1 mm to 5 mm. A size G of the microgap 58 may be a minimum size in which the filter plate is not substantially touched to the surface of the hand rail 60 and air flow is permitted inside and outside of the enclosure 2. As a result, the size of the microgap 58 is significantly smaller than the size of the entire enclosure 2. For example, a ratio of the microgap G to the length L of the filter plate is 0.1/30, that is, 1/300.

According to this embodiment, cleanliness of the hand rail can be improved because bacteria, viruses, and hand marks attached to the hand rail can be sterilized and cleaned by radicals generated by the plasma, and they can be removed.

Figure 6A:
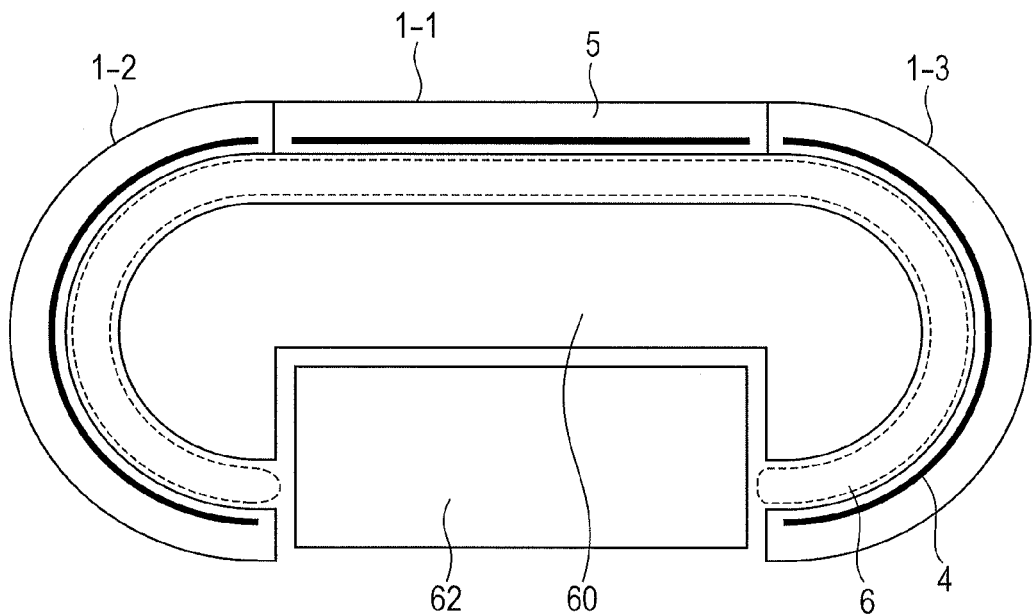
FIG. 6A is a view showing a cross sectional surface in a vertical direction to the moving direction of the hand rail for showing a modified embodiment of a discharge part of the plasma source in the first embodiment.
Figure 6B:
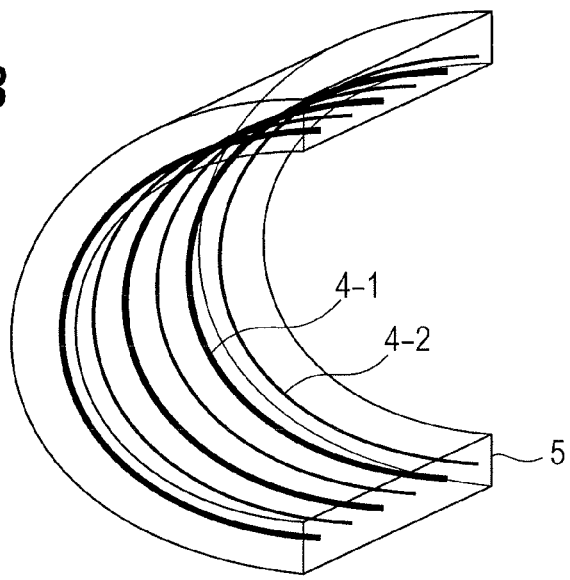
FIG. 6B is a view showing a stereoscopic structure of the discharge part in FIG. 6A.
Figure 6C:
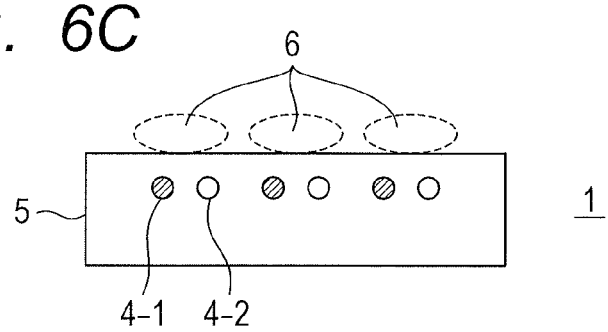
FIG. 6C is a cross-sectional view of the discharge part in FIG. 6A.

The plasma source is not limited to the plasma source having the flat-type discharge part described in the first embodiment. As shown in FIGS. 6A to 6C, the plasma source also may be constituted by combining the flat-type plasma discharge part and a curved-type plasma discharge part and having a discharge surface along the shape of the hand rail. FIG. 6A shows a cross sectional surface of the discharge part in a vertical direction to the moving direction of the hand rail. FIG. 6B shows a schematic view of a stereoscopic structure of the discharge parts 1-2 and 1-3. FIG. 6C shows a cross sectional structure of the discharge part. In this modified embodiment, the curved plasma discharge parts 1-2 and 1-3 are located in a curved part of the cross sectional surface of the hand rail 60. In other words, electrodes 4-1 and 4-2 are located in the dielectric body along the curved part of the hand rail. Plasma 6 is also generated by forming a pair of the electrodes 4-1 and 4-2 in the curved plasma source. Thereby, almost uniform plasma 6 can be generated along the surface of the hand rail. Other constitution, operation, and effect are the same as the first embodiment.

Second Embodiment

Subsequently, the second embodiment of the present invention is described. Sterilization and cleaning using oxygen radical and the like generated by plasma irradiation from the plasma source 1 cause waste of surface of the hand rail 60. Therefore, it may be desirable that a ratio of a quantity of UV light having a sterilization effect and a quantity of ions and radicals having both effects of sterilization and cleaning.

In this case, it is recommended that a slit is provided for passing the UV light and adjusting the irradiation quantity of the ions and radicals.

Figure 7A:
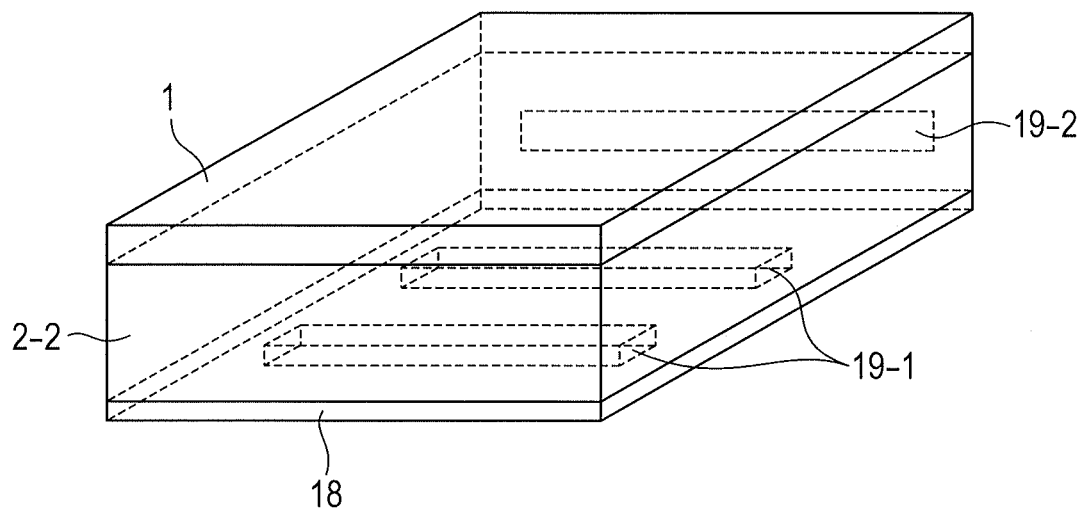
FIG. 7A is a schematic stereoscopic view of the plasma source according to a second embodiment of the present invention when a slit is attached.
Figure 7B:
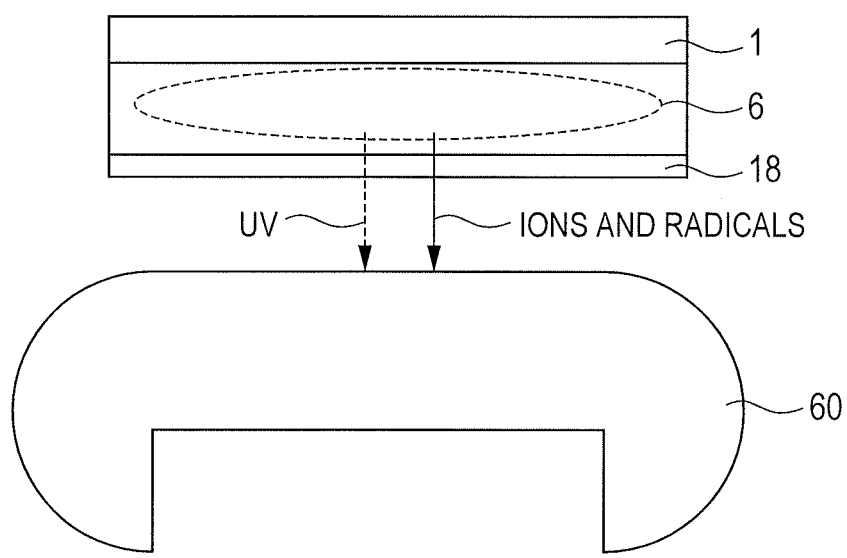
FIG. 7B is a view showing an image when the hand rail is irradiated in the second embodiment.

FIG. 7A is a schematic stereoscopic view of the plasma source when a slit is attached. FIG. 7B is a view showing an image when the hand rail is irradiated. A plasma side of the plasma source is covered with the enclosure 2-2. A UV light transparent plate 18 where slits 19-1 constituted by a UV light transparent substrate such as quartz glass are formed is located under the plasma source 1. A slit 19-2 for supplying air to the plasma source 1 is also located at the side face of the enclosure 2-2.

Thereby, sterilization treatment is performed by irradiating the hand rail 60 with UV light generated by plasma through the transparent plate 18. In addition, sterilization and cleaning treatment are performed by irradiating the hand rail with ions and radicals being effluent through the slit.

Third Embodiment

Figure 8:
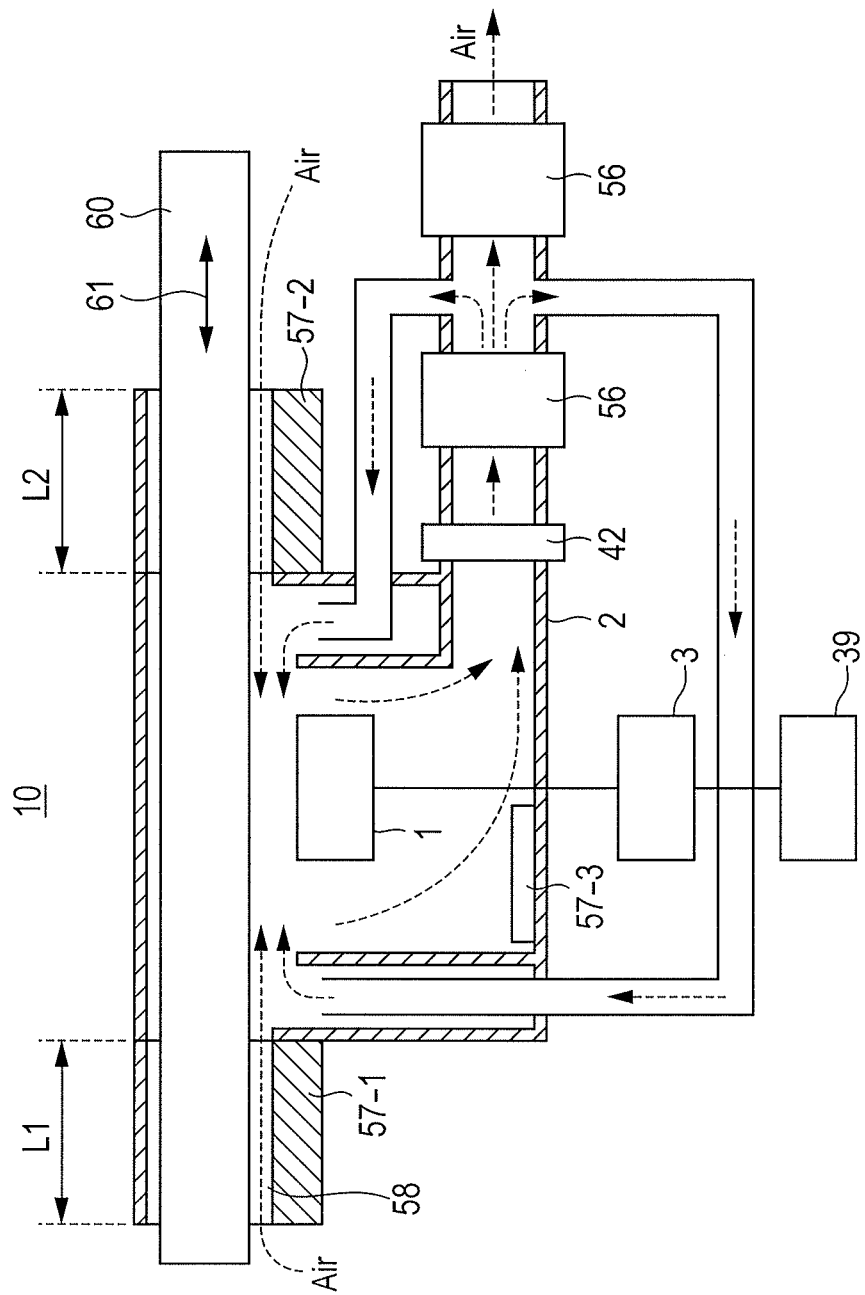
FIG. 8 is a view schematically showing entire constitution of a sterilization and cleaning device for an escalator hand rail according to a third embodiment of the present invention.

Subsequently, the third embodiment of the present invention is described using FIG. 8. In this embodiment, a function in which a part of air in the encapsulated space in the enclosure is circulated through the filter is added to the device of the first embodiment.

In other words, activated species such as oxygen radical and other volatile matters generated by plasma irradiation in the air in the enclosure collected by the fan 42 is removed through the filter 56-1 for removing them. A part of the air is circulated in the encapsulated space in the enclosure. The remaining part of the air is exhausted outside through the filter 56-2. By such a circulation function, filter performance required for the filter 56-1 or the filter 56-2 can be downgraded to some extent. Therefore, cost reduction or life lengthening of entire filters is possible. This embodiment is suitable for use environment where an attached quantity of stain on the hand rail is large.

Fourth Embodiment

Subsequently, the fourth embodiment of the present invention is described using FIG. 9 and FIG. 10. The filter can be configured more simply or the fan can be omitted depending on use of an escalator.

Figure 9:
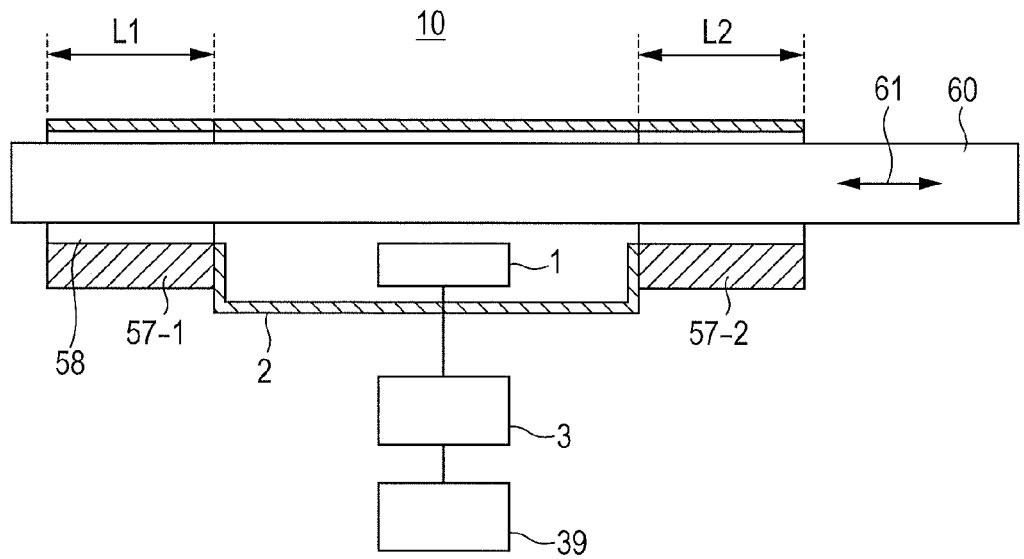
FIG. 9 is a view schematically showing a constitution example of a sterilization and cleaning device for an escalator hand rail according to a fourth embodiment of the present invention.

First, the fan 42 and the filter 56 in the device of the first embodiment are omitted in an example of FIG. 9. A pair of filter plates 57 is arranged at both sides of the enclosure 2 to a moving direction of the hand rail through the microgap 58 between the filter plates 57 and the escalator hand rail 60. Air can enter into and leave from the encapsulated space of the enclosure 2 through the microgap 58. Oxygen and nitrogen ions and radicals in air are generated by plasma in the enclosure. Bacteria and viruses attached to the surface of the hand rail 60 are detoxificated by irradiating the hand rail with these activated species. Organic matters such as hand marks attached to the hand rail are vaporized by radicals and UV light generated in plasma and heat of the plasma. Thereby, activated species, nitrogen oxides $NO_x$, detoxify bacteria and viruses, hand marks, and other volatile matters are included in the air in the enclosure 2. The activated species, the volatile matters, and the like included in the air in the enclosure are removed by the pair of filter plates 57. As a result, flying apart of undesirable substances into the atmosphere can be kept to a minimum. Since this is a natural ventilation method, sterilization and cleaning ability is slightly lower than the method of forcible ventilation method of the first embodiment. However this embodiment has an advantage that the device has the simple structure and cost of the device can be reduced.

Figure 10:
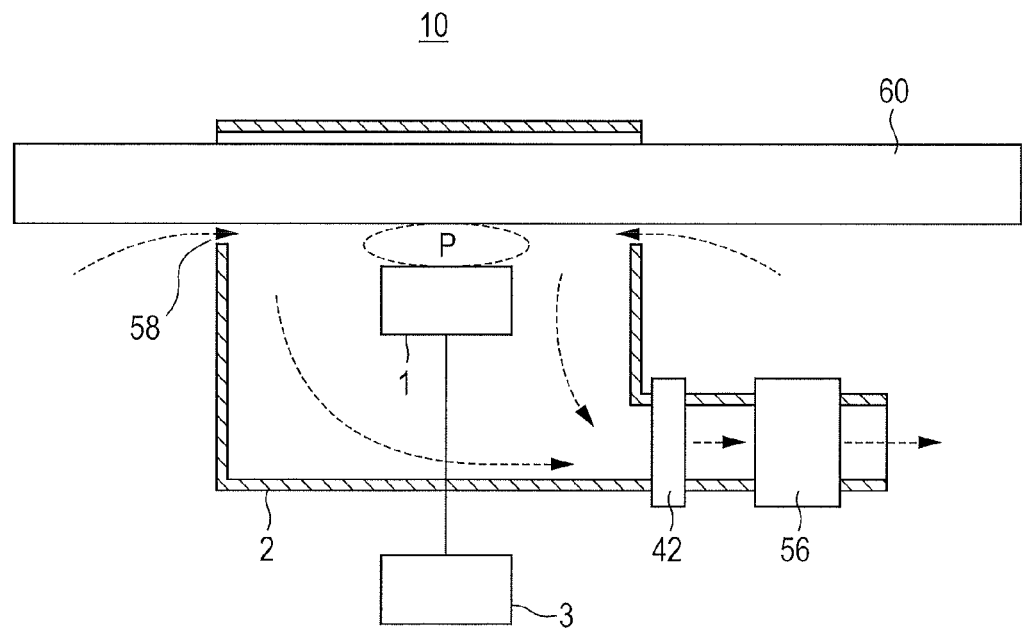
FIG. 10 is a view schematically showing another constitution example of a sterilization and cleaning device for an escalator hand rail according to a fourth embodiment of the present invention.

In an example of FIG. 10, the pair of the filter plates 57 in the device of the first embodiment is omitted. Pressure of the encapsulated space in the enclosure 2 is controlled so as to become slightly negative pressure to the surrounding atmosphere by rotating the fan 42. Thereby, air is sucked along the microgaps 58 (58-1 and 58-2) between the enclosure 2 and the hand rail 60. The activated species, the volatile matters, and the like included in the air in the enclosure are removed by the filter 56 by forcible ventilation. As a result, flying apart of the undesirable substances into the atmosphere can be kept to a minimum. When the escalator stops by power failure or other accidents, the fan 42 usually stops too. In this embodiment, a battery is added to a power source of the fan 42. Thereby, the fan 42 can continuously be operated for slight time, for example, one minute even when power is failed. Thereby, the activated species and other volatile matters remaining in the enclosure 2 are removed by the filter 56. As a result, flying apart of the undesirable substances into the atmosphere can be kept to a minimum.

Also in this embodiment, cleanliness of the hand rail can be improved because bacteria, viruses, and hand marks attached to the hand rail are sterilized and cleaned by radicals generated by plasma, and they can be removed.

Fifth Embodiment

Subsequently, as the fifth embodiment of the present invention, a plasma sterilization and cleaning treatment device including a function which performs ON/OFF control and intensity control of plasma is described using FIG. 11A or FIG. 13.

Figure 11A:
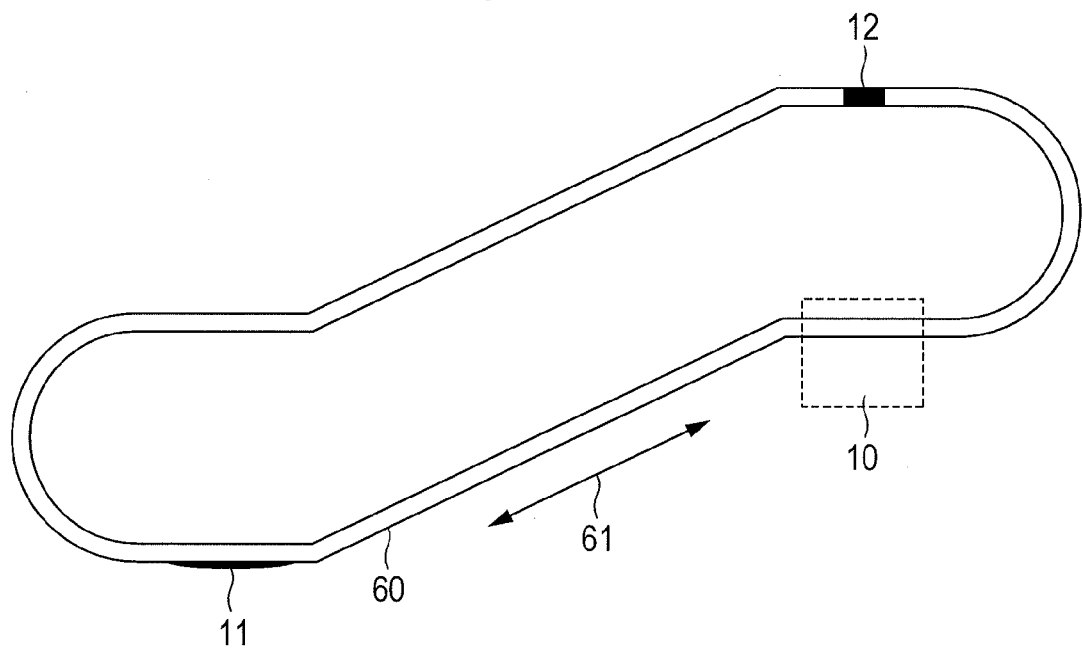
FIG. 11A is a view showing a constitution example of a hand rail according to a fifth embodiment of the present invention.
Figure 11B:
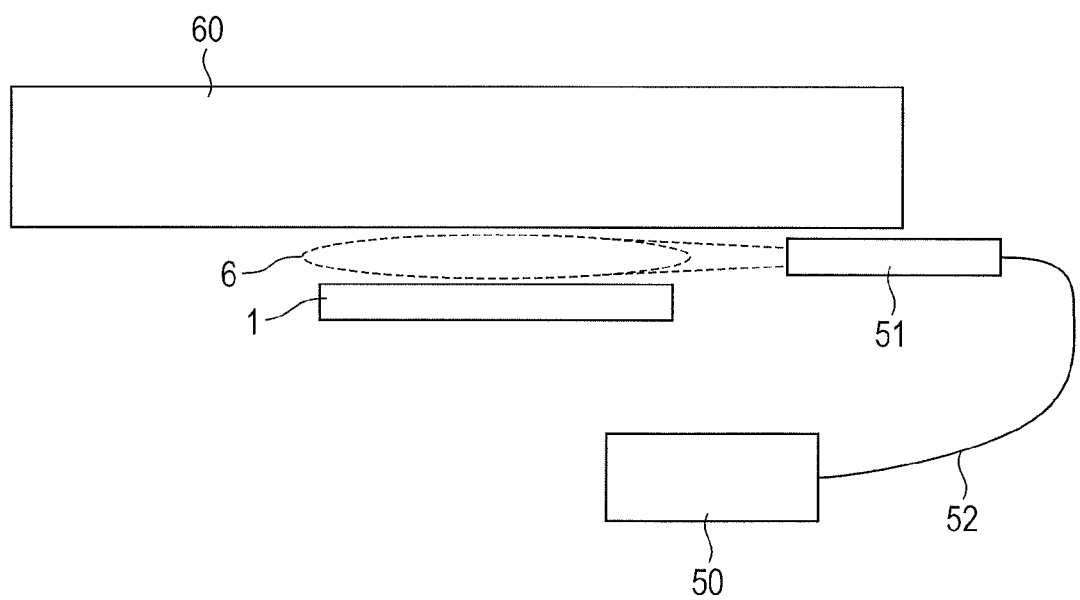
FIG. 11B is a view showing a constitution example of a marker detector in the fifth embodiment.

In this embodiment, a marker 12 for identifying a position of the hand rail 60 is located in the hand rail as shown in FIG. 11A. This marker 12 (not illustrated) can determine what part of the hand rail is currently faced to the plasma sterilization and cleaning unit 10. FIG. 11B shows a marker detector located in the plasma sterilization and cleaning unit 10. The marker detector includes a spectroscope 50 connected to the control computer, a light collect part 51, and fiber optics 52.

It is assumed that stain is particularly severe in a stained part 11 in FIG. 11A. The marker detector collects plasma light by the light collect part 51, and the collected plasma light is introduced into the spectroscope 50 through the fiber optics 52, and then an emission spectrum of the plasma is observed in a spectroscopic measurement by the spectroscope 50. At this time, the spectrum is mainly attributed to substances constituting the hand rail itself, for example, carbon, oxygen, and hydrogen, and nitrogen which are a component of air, when stain does not exist on the surface of the hand rail. On the other hand, an emission spectrum of materials included in a living body, inorganic matters, such as calcium and sodium is observed when the stain is hand marks. In other words, whether stain exists or not can be determined by comparing a measured spectrum profile with the spectrum profile with a state in which the hand rail is clean. A stained part 11 of the hand rail 60 can be detected as a stained position from a relative position of the marker 12 and the emission spectrum.

Figure 12:
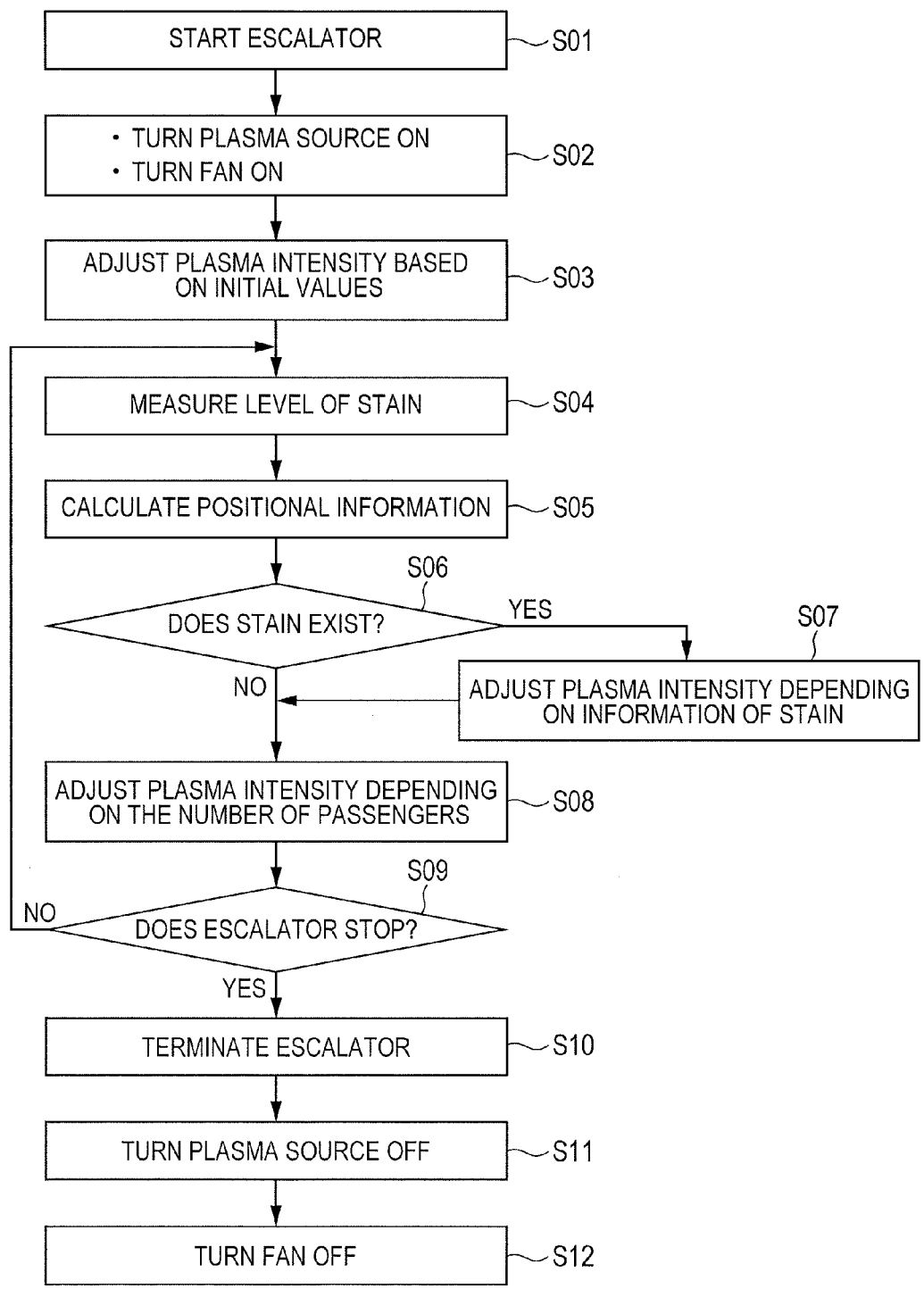
FIG. 12 is a flow chart showing an operation in the fifth embodiment.

For example, as shown in FIG. 12, control which varies intensity of plasma depending on a moved position of the hand rail is possible from a degree of stain and positional information of the stain by monitoring level of the stain.

Figure 13A:
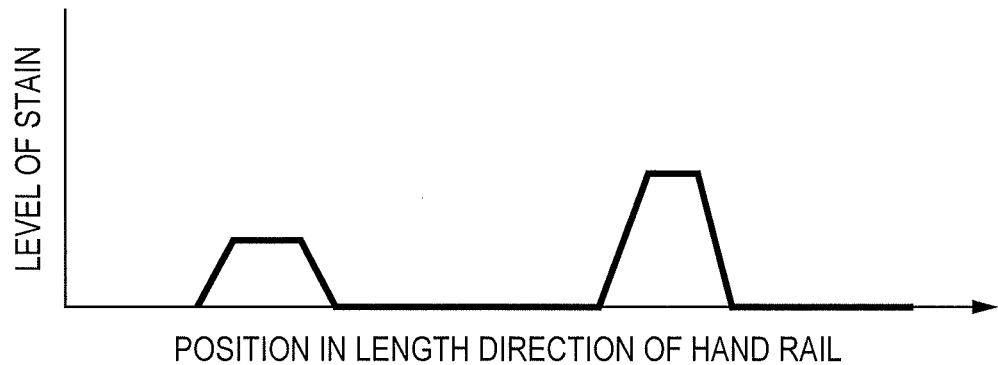
FIG. 13A is a view showing a plasma control method in the fifth embodiment.
Figure 13B:
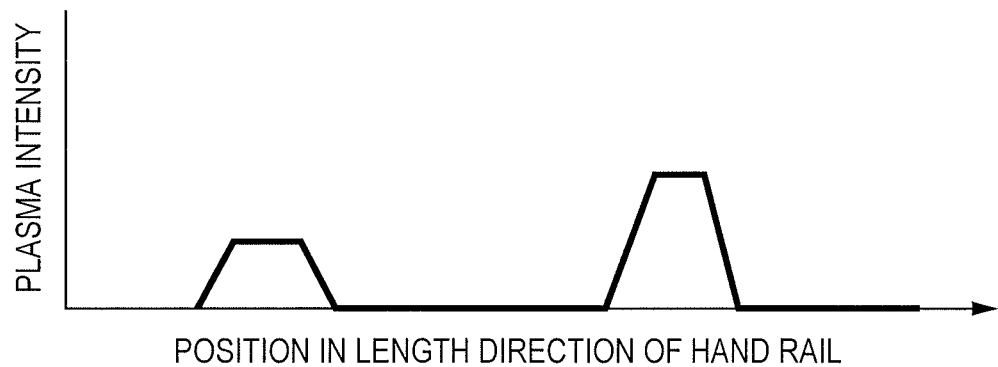
FIG. 13B is a view showing a plasma control method in the fifth embodiment.

FIG. 12 is an outline of the process performed by the control computer, that is, a flow chart showing an operation in the fifth embodiment. The escalator starts (S01). The fan 42 is made to start as well as plasma discharge is made to start by turning on the plasma source (S02). Then, intensity of the plasma is adjusted based on default values (S03). Stain level of the hand rail is measured by the marker detector (S04), and positional information of the hand rail is calculated (S05). When the stain is detected (S06), intensity and irradiation position of the plasma is adjusted depending on the information of the stain (S07). For example, when the positional information of the stain is obtained as data from an emission spectrum as shown in FIG. 13A, control which varies plasma intensity and area of plasma discharge is effective as shown FIG. 13B. Generally, stain is varied depending on the number of passengers on the escalator. Therefore, information of the number of passengers is separately obtained by sensors or other means, and the intensity of the plasma is adjusted depending on the number of passengers (S08). In other words, for example, control which varies the intensity of the plasma and the area of plasma discharge depending on the number of passengers on the escalator is also effective when a quantity of the stain is small. When the condition becomes to stop operation of the escalator (S09), the escalator is made to stop (S10) and the plasma source is made to turn off (S11). After passing predetermined time (for example, one minute) from the termination of the plasma discharge, the fan 42 is made to stop (S12).

According to the embodiments of the present invention, cleanliness of the hand rail can be improved because bacteria, viruses, and hand marks attached to the hand rail are sterilized and cleaned by radicals generated by plasma, and they can be surely removed. For example, this elevator is suitable for an environment such as a general hospital where a large number of people including patients uses and significantly high level of cleanliness is required.

What is claimed is:

1. A plasma sterilization and cleaning treatment device for an escalator, comprising:
    a plasma source having a planar discharge part arranged along a surface shape of an escalator hand rail and along a moving direction of the hand rail;
    an enclosure for housing the plasma source in encapsulated space;
    a pair of inlet parts located in the enclosure so as to communicate the encapsulated space to the outside atmosphere along the moving direction of the hand rail;
    filter plates arranged at the pair of the inlet parts, having a shape along a cross sectional surface shape of the hand rail, and having a microgap between the filter plate and the surface of the hand rail; and
    a power source for the plasma source,
    wherein the plasma source generates plasma close to the surface of the hand rail in an atmospheric pressure atmosphere; and
    wherein the filter plate has a filter for removing radicals generated in the space by the plasma and organic matters on the hand rail removed by the plasma.

2. The plasma sterilization and cleaning treatment device for the escalator according to claim 1,
    wherein the plasma source comprises a discharge plate constituting a planar discharge part;
    wherein the discharge plate is constituted by a dielectric body made of a ceramic material and a pair of electrodes arranged inside of the dielectric body;
    wherein the discharge plate has a length corresponding to a width of the hand rail;
    wherein the pair of the electrodes have a structure in which a plurality of insulated comb-shaped electrodes are alternately arranged parallel to each other in a rectangular region;
    wherein the pair of the electrodes have a length corresponding to a width of the hand rail; and
    wherein the plasma is generated close to the surface of the dielectric body by dielectric barrier discharge by applying high frequency radiation between the pair of the electrodes so that the electrodes have different polarity each other.

3. The plasma sterilization and cleaning treatment device for the escalator according to claim 2,
    wherein the plasma source is comprised of a plurality of the discharge plate constituting the planar discharge part and the plurality of the discharge plate are located so as to cover the entire outer surface of the hand rail except a part of a guide.

4. The plasma sterilization and cleaning treatment device for the escalator according to claim 3,
    wherein the plasma source is located so that a plurality of flat-type discharge plates are arranged to cover the entire outer surface of the hand rail except the part of the guide.

5. The plasma sterilization and cleaning treatment device for the escalator according to claim 3,
    wherein the plasma source is constituted by combining the at least one flat-type plasma discharge part and at least one curved-type plasma discharge part and having a discharge surface along the shape of the hand rail.

6. The plasma sterilization and cleaning treatment device for the escalator according to claim 1,
    wherein a length L of the each filter plate is set to a relation of:

$$L \propto V \cdot G,$$

where a moving speed of the hand rail is V and a size of the microgap is G.

7. The plasma sterilization and cleaning treatment device for the escalator according to claim 6,
    wherein the microgap is 1 mm to 5 mm.

8. The plasma sterilization and cleaning treatment device for the escalator according to claim 1,
    wherein the filter plate comprises activated carbon and an ozone decomposition catalyst for absorbing activated species and removed and vaporized organic matters.

9. The plasma sterilization and cleaning treatment device for the escalator according to claim 8,
    wherein the filter plates are divided into a plurality of filter plates to a moving direction of the hand rail and are constituted so as to have different type of the absorbent and the catalyst located facing to the hand rail, surface roughness, or porosity.

10. A plasma sterilization and cleaning treatment device for an escalator comprising:
    a plasma source having a planar discharge part arranged along a surface shape of an escalator hand rail and along a moving direction of the hand rail;
    an enclosure for housing the plasma source in encapsulated space;
    a pair of inlet parts located in the enclosure so as to communicate the encapsulated space and the outside atmosphere along the moving direction of the hand rail;
    a fan for generating relatively negative pressure in the enclosure;
    an exhaust path located in the enclosure so as to communicate the encapsulated space to the outside atmosphere;
    filter plates arranged at the pair of the inlet parts, having a shape along a cross sectional surface shape of the hand rail, and having a microgap between the filter plate and the surface of the hand rail;
    a filter box arranged in the exhaust path; and
    a power source for the plasma source,
    wherein the plasma source generates plasma close to the surface of the hand rail in an atmospheric pressure atmosphere; and
    wherein the filter plate and the filter box have filters for removing radicals generated in the space by the plasma and organic matters on the hand rail removed by the plasma.

11. The plasma sterilization and cleaning treatment device for the escalator according to claim 10, wherein the plasma source comprises a discharge plate constituting a planar discharge part;

wherein the discharge plate is constituted by a dielectric body made of a ceramic material and a pair of electrodes arranged inside of the dielectric body;

wherein the discharge plate has a length corresponding to a width of the hand rail; and wherein the plasma source is comprised of a plurality of the discharge plate constituting the planar discharge part and the plurality of the discharge plate are located so as to cover the entire outer surface of the hand rail except a part of a guide.

12. The plasma sterilization and cleaning treatment device for the escalator according to claim 11, wherein the pair of the electrodes have a structure in which a plurality of insulated comb-shaped electrodes are alternately arranged parallel to each other in a rectangular region;

wherein the pair of the electrodes have a length corresponding to a width of the hand rail; and wherein the plasma is generated close to the surface of the dielectric body by dielectric barrier discharge by applying high frequency radiation between the pair of the electrodes so that the electrodes have different polarity each other.

13. The plasma sterilization and cleaning treatment device for the escalator according to claim 12, wherein the plasma source is located so that a plurality of flat-type discharge plates are arranged to cover the entire outer surface of the hand rail except the part of the guide.

14. The plasma sterilization and cleaning treatment device for the escalator according to claim 12, wherein the plasma source is constituted by combining the at least one flat-type plasma discharge part and at least one curved-type plasma discharge parts and having a discharge surface along the shape of the hand rail.

15. The plasma sterilization and cleaning treatment device for the escalator according to claim 10, wherein a length L of the each filter plate is set to a relation of:

$$L \propto V \cdot G,$$

where a moving speed of the hand rail is V and a size of the microgap is G.

16. The plasma sterilization and cleaning treatment device for the escalator according to claim 10, wherein a second filter unit for removing activated species and volatile matters included in air collected by the fan is comprised in the encapsulated space.

17. The plasma sterilization and cleaning treatment device for the escalator according to claim 10, wherein a third filter unit for removing activated species and volatile matters included in the air collected by the fan is comprised in the exhaust path and an upstream side of the filter box; and wherein air stream is divided in a downstream side of the third filter unit, and one of the air stream is blown out close to the plasma source, and the other is exhausted to the atmosphere through the second filter unit.

18. The plasma sterilization and cleaning treatment device for the escalator according to claim 10, wherein a UV light transparent plate with a slit constituted by quartz glass for passing through UV light is located under the plasma source.

19. An escalator comprising:

a hand rail for the escalator;

a plasma sterilization and cleaning treatment device for the hand rail; and a control computer, wherein the plasma sterilization and cleaning treatment device comprises:

a plasma source having a planar discharge part arranged along a surface shape of the hand rail and along a moving direction of the hand rail;

an enclosure for encapsulating the plasma source in encapsulated space;

a pair of inlet parts located in the enclosure so as to communicate the encapsulated space and the outside atmosphere along the moving direction of the hand rail;

filter plates arranged at the pair of the inlet parts, having a shape along a cross sectional surface shape of the hand rail, and having a microgap between the filter plate and the surface of the hand rail; and a power source for the plasma source, wherein the plasma source generates plasma close to the surface of the hand rail in an atmospheric pressure atmosphere; and wherein the filter plate has a filter for removing radicals generated in the space by the plasma and organic matters on the hand rail removed by the plasma.

20. The escalator according to claim 19, wherein the control computer monitors a level of stain on the hand rail and controls the power source of the plasma source in order to increase intensity of the plasma to a stained part of the hand rail from a degree of the stain and positional information of the stain.

* * * * *